US005681550A

United States Patent [19]
Rubino

[11] Patent Number: 5,681,550
[45] Date of Patent: Oct. 28, 1997

[54] WATER BORNE NAIL POLISH

[76] Inventor: Michael R. Rubino, 2007 Gardner Rd., Wall, N.J. 07719

[21] Appl. No.: 754,201

[22] Filed: Nov. 20, 1996

Related U.S. Application Data

[63] Continuation-in-part of Ser. No. 305,974, Sep. 16, 1994, abandoned.
[51] Int. Cl.$^6$ ................................................. A61K 7/043
[52] U.S. Cl. ............................................. 424/61; 424/401
[58] Field of Search ...................................... 424/61, 401

[56] References Cited

U.S. PATENT DOCUMENTS

| | | | |
|---|---|---|---|
| 4,712,571 | 12/1987 | Remz et al. | 424/61 |
| 5,066,484 | 11/1991 | Castrogiovanni et al. | 424/61 |
| 5,120,529 | 6/1992 | Koch et al. | 424/61 |
| 5,284,885 | 2/1994 | Nehra | 524/31 |
| 5,290,543 | 3/1994 | Ounanian et al. | 424/61 |
| 5,422,361 | 6/1995 | Munayyer et al. | 514/408 |
| 5,503,754 | 4/1996 | Counts et al. | 252/8.57 |

*Primary Examiner*—Amy Hulina
*Attorney, Agent, or Firm*—Peter A. Borsari

[57] ABSTRACT

The present invention relates to a water-borne nail polish formulation which is non-flammable, non-toxic and is practically odorless comprising the use of water-dispersible ingredients. The water-based nail polish formulation comprises from about 10 to about 80%/wt. of a water-dispersible aliphatic urethane, from about 1.0 to about 10.0%/wt. of a hardening agent, from about 3.0 to about 10.0%/wt. of a plasticizer agent, and the balance being a isopropyl alcohol:water solvent mixture. The nail polish formulation of the present invention eliminates the use of any noxious or toxic components, such as nitrocellulose, toluene, styrene, MEK and the like.

18 Claims, No Drawings

WATER BORNE NAIL POLISH

This application is a continuation-in-part of U.S. patent application Ser. No. 08/305,974, filed Sep. 16, 1994 now abandoned.

FIELD OF INVENTION

The present invention relates to a water-based nail polish comprising a water dispersible aliphatic urethane dissolved in an isopropyl:water solvent mixture, a hardening agent, a plasticizing agent and a thickening agent.

BACKGROUND OF THE INVENTION

Nail polish compositions generally in use today are those commonly referred to as lacquer nail polishes. These lacquer nail polish compositions usually are quite flammable, emit noxious fumes and comprise a number of compounds which are considered toxic, including, for example, formaldehyde and toluene, the latter of which is thought to be a cause of birth defects. For example, U.S. Pat. No. 5,102,654 to Castrogiovanni et al. discloses a single phase lacquer emulsion nail enamel comprising a lacquer phase having about 5-25% nitrocellulose, about 10-70% of an active organic solvent system to dissolve the nitrocellulose, comprising glycol ethers, ketones (e.g. methyl ethyl ketone or MEK), toluene, ethyl acetate and/or butyl acetate, about 2-15% of a $C_{1-6}$ organic alcohol, about 0.5-10% of a resin and about 0.1-10% of a plasticizer, such as camphor. U.S. Pat. No. 5,290,543 to Ounanian et al. discloses a long wearing enamel topcoat comprising nitrocellulose, plasticizers, such as the phthalates and/or camphor, and a mixture of solvents, such as toluene, ethyl acetate, butyl acetate and MEK.

Attempts have been made to provide a nail polish composition which contains neither nitrocellulose nor the noxious solvents required to dissolve the nitrocellulose. One such attempt is illustrated in U.S. Pat. No. 5,120,529 to Koch et al. which discloses a water-based nail polish comprising a polyurethane and polyurethane-acrylate copolymer in dispersed form as a binder, a thickening agent and the addition of one or several natural and/or synthetic resins for increased hardness of the dried nail polish. Koch et al. disclose that the preferred hardener is an acrylate-styrene polymer, despite the fact that styrenes have been found to be toxic in cosmetic formulations.

The present invention provides an advance in the water-based nail polish art by providing a formulation comprising a water-dispersible aliphatic urethane dissolved in an isopropyl alcohol:water solvent. Significantly, the present formulation does not require the use of any noxious or toxic components, such as nitrocellulose, toluene, styrene, MEK and the like.

SUMMARY OF THE INVENTION

Accordingly, it is an object of the present invention to provide a water-based nail polish formulation.

It is another object of the present invention to provide a water-based nail polish formulation which does not require the use of noxious or toxic solvents, such as toluene, MEK, ethyl acetate, butyl acetate and the like.

It is still another object of the present invention to provide a water-based nail polish formulation which does not require the use of nitrocellulose.

It is a further object of the present invention to provide a water-based nail polish formulation wherein the binder is a water-dispersible, cross-linkable aliphatic urethane.

It is an additional object of the present invention to provide a water-based nail polish formulation which requires only water-based materials.

It is yet another object of the present invention to provide a water-based nail polish formulation which is essentially non-toxic.

It is a further object of the present invention to provide a water-based nail polish formulation which is non-flammable.

If is another objection of the present invention to provide a water-based nail polish formulation which does not produce noxious fumes and is practically odorless.

Additional objects, advantages and novel features of the invention will be set forth in part in the description which follows, and in part will become apparent to those skilled in the art upon examination of the following specification or may be learned by practice of this invention.

These and other objects of the invention, as embodied and broadly described herein, are achieved by providing a water-based nail polish formulation comprising a water-dispersible aliphatic urethane, a hardening agent and a plasticizer dispersed in an isopropyl alcohol/water solvent mixture.

DETAILED DESCRIPTION

The present invention relates to a water-borne nail polish formulation comprising a water-dispersible aliphatic urethane dispersed in an isopropyl:water solvent mixture. More specifically, the nail polish formulation comprises from about 10 to about 80%/wt. of a water dispersible aliphatic urethane, from about 1.0 to about 10.0%/wt. of a hardening agent, from about 0.5 to about 10.0%/wt. of a plasticizing agent, with the balance being a isopropyl alcohol:water solvent mixture. Aliphatic urethanes are well known in the prior art. Suitable aliphatic urethanes include, for example, "Aliphatic UE96" by By-Chem Corporation, "UT-1080 and UT-1082" by Soluol Chemical Company, "Urethane #PS3856" by Kep-tite Corporation, "Aliphatic UT-#57, UT-27 and UT-#7407" by Union Specialists, "UT water-borne asticin finflex PUM" by BASF Corporation, and "Aliphatic UT#898" by Sanncor Corporation. The aliphatic urethane is dissolved in an isopropyl alcohol:water solvent. The ratio of isopropyl alcohol to water is 10 to 90 parts alcohol to 90 to 10 parts water. Preferably the ratio of isopropyl alcohol to water is 50:50. The amount of isopropyl alcohol:water solvent used in the present formulation ranges in the amount of about 10.0 to about 60.0%/wt. Preferably, from about 10 to about 25.0%/wt. of the isopropyl alcohol:water solvent mixture is present in the formulation.

The water-borne nail polish formulation further comprises from about 1.0 to about 10.0%/wt. of a hardening agent, preferably from about 1.0 to about 5.0%/wt. and more preferably from about 2.0 to about 3.0%/wt. Suitable hardening agents for use in the present invention include compounds which cross-link with the aliphatic urethane, such as epoxy resins and urethane polymers. Particularly preferred hardeners include, for example, epoxy resins, such as Witco Company's "Witcobond XW" and urethanes, such as "PM Hardener" by BASF Corporation. The addition of the hardening agent prevents the dried nail polish from chipping, scratching, peel and cracking, and provides resistance to the enamel solution from coming off. Other hardeners which may be used in the present formulation include acrylic hardeners, such as "Primal WA-91 aqueous wax hardener" by Rohm & Haas and BYK Chemical Company's "#301–344 acrylic resins" and acrylic latexes, such as B. F. Goodrich's "flame resistance resins #26256 and #26172."

Preferably, the hardener is an epoxy resin, particularly Witco Company's "Witcobond XW" which is described as being an epoxy resin aqueous dispersion.

The water-borne nail polish composition also comprises from about 0.5 to about 10.0%/wt. of a plasticizer to increase the flowability and leveling of the coating. Suitable plasticizers include, for example, monomeric plasticizers, such as phthalates, adipates, sebacates, glycolates, non-ionic polymers, castor oil and the like. Preferred plasticizers include, the phthalates, examples of which include Dow Chemical Company's "DOP waterborne plasticizer" and Dow Chemical Company's "160 waterborne plasticizer." More preferably, the plasticizer is a nonionic surfactant polymer, such as alkylaryloxy polyalkoxy alcohols, such as nonylphenoxy polypropoxy alcohol or cresyloxy polypropoxy alcohol. The latter two examples are sold commercially under the trade names "Paraplex WP-1" by Rohm & Haas, Inc. and "Plastilit 3060" by BASF, AG, respectively. Most preferably, the plasticizing agent employed in the present formulation is Rohm & Haas' "Paraplex WP-1"

The water-borne nail polish formulation of the present invention additionally may comprise a from about 5.0 to about 25.0%/wt. of a thickening agent. Suitable thickening agents include, for example, natural and synthetic polymers, such as casein, natural gum polymers, cellulosic polymers, such as B. F. Goodrich's "CarboPol" and Union Carbide Chemical Company's "Methocul", and acrylic polymers and copolymers, such as Rohm & Haas Chemical Company's "RM Rhoplex #4", "RM Rhoplex #5", and an acrylic polymer by Rohm & Haas designated "Acrysol thickener-TT615".

The water-borne nail polish formulation of the present invention additionally may comprise from about 0.05 to about 10.0%/wt. of a penetrating agent in order to drive the finish into the nail. It has been discovered that conventional non-toxic penetrating agents well known in the leather finishing field are exceptionally well suited for use in the water-borne nail polish of the present invention. Although the present invention contemplates the use of any non-toxic leather finishing penetrating agent to drive the nail polish finish into the nail, suitable leather penetrating agents suitable for use in the present invention include, for example, Henkel Corporation's mixture of alkylpolyglycosides as described in U.S. Pat. No. 5,503,754 to Counts et al., issued Apr. 2, 1996, the disclosure of which is incorporated herein by reference. These alkylpolyglycosides are disclosed as being substantially free of volatile organic compounds. Other suitable leather penetrating agents include BASF Corporation's "Astacin Bottom UH" which is described as being methyl-2-pyrrolidine solvent which is diluted 50% in water and Rohm & Haas' "AOS Primal Penetrator SF10" which is described as being an aqueous solution of an alkylaryl polyether phosphate ester. Preferably, the penetrating agent employed in the present formulation is BASF Corporation's "Astacin Bottom UH".

The nail polish formulation optionally may contain a variety of non-essential additional constituents such as adhesives and adhesive promoters, drying accelerators, preservatives, humectants, vitamins, herbal extracts, protein hydralyzates, UV absorbants & sunscreens and, of course, cosmetically-acceptable water-dispersible dyes and colorants.

The following examples are provided merely to illustrate the present invention, and it is to be understood the invention is not limited thereto. All amounts of the various ingredients in the examples and elsewhere in the specification are by weight unless otherwise specified.

EXAMPLE 1

Clear Top Coat

The clear top coat shown in the following table was prepared by mixing 400 parts of Formula A and 300 parts of Formula B.

| Component | Formula A %/wt. | Formula B %/wt. |
|---|---|---|
| #96 waterborne aliphatic urethane | 40.00 | 30.00 |
| WP-1 plasticizer | 0.05 | 0 |
| Asticin bottom UH penetrator | 0.05 | 0 |
| Dow Corning Adhesion Promoter | 1.5 | 0 |
| Epoxy Hardener | 1.5 | 0 |
| Isopropyl alcohol | 0 | 5 |
| Isopropyl alcohol:water (50:50) | balance | 0 |

*The Dow Corning adhesion promoter is described as a silicone additive

The resulting water based-nail polish exhibited a clear appearance and was practically odorless. The polish was applied to a set of nails which had been cleaned of all previously applied polish, sanded lightly with a file and re-cleaned to remove any file dust. After application of the first coat, the nail polish was allowed to dry for about five (5) minutes and a second coating was applied to the nails. The polished nails exhibited a beautiful high gloss appearance.

EXAMPLE 2

Clear Top Coat

| Component | %/wt. |
|---|---|
| #96 waterborne aliphatic urethane | 80.0 |
| WP-1 plasticizer | 3.0 |
| Witcobond XW epoxy hardener | 2.0 |
| Asticin bottom UH penetrator | 1.0 |
| Isopropyl alcohol:water (50:50) | balance |

The resulting water based-nail polish exhibited a clear appearance and was practically odorless. The polish was applied to a set of nails which had been cleaned of all previously applied polish, sanded lightly with a file and re-cleaned to remove any file dust. After application of the first coat, the nail polish was allowed to dry for about five (5) minutes and a second coating was applied to the nails. The polished nails exhibited a beautiful high gloss appearance.

In an alternate embodiment of the present invention, the aliphatic urethane component may be partially substituted with a urethane-acrylic copolymer. Suitable urethane-acrylics include, for example, "UT and Acrylic combined #43, by Rohm-Tech, "UT and Acrylic combined #7-1382" by Rohm & Haas, and Waterborne Acrylic #137 by Rohm-Tech. Up to about 50%/wt. of the aliphatic urethane may be substituted by the urethane-acrylics. Additionally, the aliphatic urethane may be partially substituted by an acrylic polymer. Suitable acrylic polymers include, for example, Rohm & Haas' "Rhoplex WL-92", described as being an acrylic emulsion of an acrylic polymer in aqua ammonia Rohm & Haas' "#92 Acrylic" and "#96 Acrylic". Up to about 25%/wt. of the aliphatic urethane may be substituted by the acrylic polymer. The following examples are provided to illustrate the alternative embodiment of the present invention. All amounts of the various ingredients in the examples and elsewhere in the specification are by weight unless otherwise specified.

EXAMPLE 3

Clear Top Coat

| Component | %/wt. |
|---|---|
| #96 waterborne aliphatic urethane | 40.0 |
| #82 waterborne aliphatic urethane | 20.0 |
| #92 waterborne acrylic | 20.0 |
| WP-1 plasticizer | 1.5 |
| Asticin bottom UH penetrator | 0.1 |
| Casein | 1.5 |
| Isopropyl alcohol:water (50:50) | balance |

The resulting water based-nail polish exhibited a clear appearance and was practically odorless. The polish was applied to a set of nails which had been cleaned of all previously applied polish, sanded lightly with a file and re-cleaned to remove any file dust. After application of the first coat, the nail polish was allowed to dry for about five (5) minutes and a second coating was applied to the nails. The polished nails exhibited a beautiful high gloss appearance.

EXAMPLE 4

Clear Urethane Acrylic Polish

| Component | %/wt. |
|---|---|
| #82 waterborne aliphatic urethane | 50.0 |
| #92 waterborne acrylic | 20.0 |
| WP-1 plasticizer | 3.0 |
| Asticin bottom UH penetrator | 1.5 |
| Isopropyl alcohol:water (50:50) | balance |

The resulting water based-nail polish exhibited a clear appearance and was practically odorless. The polish was applied to a set of nails which had been cleaned of all previously applied polish, sanded lightly with a file and re-cleaned to remove any file dust. After application of the first coat, the nail polish was allowed to dry for about five (5) minutes and a second coating was applied to the nails. The polished nails exhibited a beautiful high gloss appearance.

While particular embodiments of the invention have been described, it will be understood, of course, that the invention is not limited thereto, and that many obvious modifications and variations can be made, and that such modifications and variations are intended to fall within the scope of the appended claims.

What is claimed is:

1. A non-toxic water-based nail polish formulation comprising:

(a) from about 10.0 to about 80.0%/wt. of a water-dispersible aliphatic urethane;

(b) from about 0.5 to about 10.0%/wt. of a hardening agent;

(c) from about 3.0 to about 10.0%/wt. of a plasticizer; and (d) An effective amount of a non-toxic leather finishing penetrating agent sufficient to drive said nail polish into the nail, said penetrating agent selected from the group consisting of alkylpolyglycosides, an alkylaryl polyether phosphate ester and methyl-2-pyrrolidone;

(e) the balance being an isopropyl:water solvent mixture.

2. The water-based nail polish formulation according to claim 1, further comprising from about 0.5 to about 10.0%/wt. of a thickening agent.

3. The water-based nail polish formulation according to claim 1, comprising from about 0.5 to about 10.0%/wt. of said penetrating agent.

4. The water-based nail polish formulation according to claim 1, wherein said hardening agent is an epoxy resin.

5. The water-based nail polish formulation according to claim 1, wherein said plasticizer is a non-ionic surfactant polymer.

6. The water-based nail polish formulation according to claim 5, wherein said plasticizer is nonylphenoxy polypropoxy alcohol.

7. The water-based nail polish formulation according to claim 2, wherein said thickening agent is a natural or synthetic polymer selected from the group consisting of casein, cellulosic polymers, acrylic polymers and mixtures thereof.

8. The water-based nail polish formulation according to claim 1, wherein up to 50%/wt. of said aliphatic urethane is partially substituted with a urethane-acrylic resin.

9. The water-based nail polish formulation according to claim 1, wherein up to 25%/wt. of said aliphatic urethane is partially substituted with an acrylic polymer.

10. A non-toxic water-based nail polish formulation comprising:

(a) from about 10.0 to about 80.0%/wt. of a water-dispersible aliphatic urethane;

(b) from about 0.5 to about 10.0%/wt. of a hardening agent;

(c) from about 3.0 to about 10.0%/wt. of a plasticizer;

(d) from about 0.5 to about 10.0%/wt. of a thickening agent;

(e) from about 1.0 to about 10.0%/wt. of a leather finishing penetrating agent which functions to drive the finish into the nail, said penetrating agent selected from the group consisting of alkylpolyglycosides, an alkylaryl polyether phosphate and methyl-2-pyrrolidone; and (f) the balance being an isopropyl:water solvent mixture.

11. The water-based nail polish formulation according to claim 10, wherein said hardening agent is an epoxy resin.

12. The water-based nail polish formulation according to claim 1, wherein said plasticizer is a non-ionic surfactant polymer.

13. The water-based nail polish formulation according to claim 12, wherein said plasticizer is nonylphenoxy polypropoxy alcohol.

14. The water-based nail polish formulation according to claim 11, wherein said thickening agent is a natural or synthetic polymer selected from the group consisting of casein, cellulosic polymers, acrylic polymers and mixtures thereof.

15. The water-based nail polish formulation according to claim 11, wherein up to 50%/wt. of said aliphatic urethane is partially substituted with a urethane-acrylic resin.

16. The water-based nail polish formulation according to claim 11, wherein up to 25%/wt. of said aliphatic urethane is partially substituted with an acrylic polymer.

17. The water-based nail polish formulation according to claim 1, wherein said penetrating agent is methyl-2-pyrrolidine.

18. The water-based nail polish formulation according to claim 11, wherein said penetrating agent is methyl-2-pyrrolidine.

* * * * *